US008798771B2

(12) United States Patent  
Casset et al.

(10) Patent No.: US 8,798,771 B2  
(45) Date of Patent: Aug. 5, 2014

(54) IMPLANTABLE CARDIAC PROSTHETIC FOR RESYNCHRONIZATION BY BIVENTRICULAR PACING USING REVERSE REMODELING

(75) Inventors: Cyrille Casset, Saint-Selve (FR); Melanie Heurteau, Antony (FR)

(73) Assignee: Sorin CRM S.A.S., Clamart Cedex (FR)

( * ) Notice: Subject to any disclaimer, the term of this patent is extended or adjusted under 35 U.S.C. 154(b) by 106 days.

(21) Appl. No.: 13/442,754

(22) Filed: Apr. 9, 2012

(65) Prior Publication Data

US 2012/0259379 A1  Oct. 11, 2012

(51) Int. Cl.  
*A61N 1/365* (2006.01)  
*A61N 1/368* (2006.01)  
*A61B 5/00* (2006.01)  
*A61N 1/362* (2006.01)

(52) U.S. Cl.  
CPC ............ *A61N 1/3684* (2013.01); *A61N 1/3682* (2013.01); *A61N 1/3688* (2013.01); *A61N 1/3622* (2013.01); *A61B 5/6869* (2013.01); *A61B 5/686* (2013.01)  
USPC ................... 607/123; 607/9; 607/17; 607/18; 607/19; 607/115; 607/116; 607/119; 607/122; 600/508; 600/509; 600/513; 600/527

(58) Field of Classification Search  
CPC ... A61N 1/3682; A61N 1/3684; A61N 1/368; A61N 1/36585; A61N 1/3702; A61N 1/3686; A61N 1/3688; A61N 1/365; A61N 1/37; A61N 1/37241; A61N 1/36167; A61N 1/36507; A61B 5/6869; A61B 5/686; A61B 5/0402; A61B 5/0452; A61B 5/0031; A61B 5/02; A61B 5/024; A61B 5/0538; A61M 2230/04  
USPC .......... 607/9, 17–19, 115–116, 119, 122–123; 600/508–509, 513, 527  
See application file for complete search history.

(56) References Cited

U.S. PATENT DOCUMENTS

| 5,304,208 | A | 4/1994 | Inguaggiato et al. |
| 6,556,866 | B2 | 4/2003 | Dal Molin et al. |
| 7,483,740 | B2 * | 1/2009 | Ripart ............... 607/9 |
| 7,664,547 | B2 | 2/2010 | Plicchi et al. |
| 2002/0161410 | A1 | 10/2002 | Kramer et al. |
| 2007/0179542 | A1 | 8/2007 | Prakash et al. |
| 2007/0293736 | A1 | 12/2007 | Casset |
| 2009/0157134 | A1 | 6/2009 | Ziglio et al. |

FOREIGN PATENT DOCUMENTS

| EP | 0515319 A2 | 11/1992 |
| EP | 1108446 A1 | 6/2001 |
| EP | 1736203 A1 | 12/2006 |
| EP | 1 867 360 | 12/2007 |
| EP | 2070562 A1 | 6/2009 |

OTHER PUBLICATIONS

Foreign Search Report (Annexe Au Rapport De Recherche Preliminaire Relatif A La Demande De Brevet Francais No. FR 1152971 FA 749802), Oct. 28, 2011.

* cited by examiner

*Primary Examiner* — Deborah Malamud  
(74) *Attorney, Agent, or Firm* — Foley & Lardner LLP

(57) ABSTRACT

Improving cardiac response in terms of pressure, ejected volume, and filling and ejection times by cardiac reverse remodelling, including temporary, occasionally harmful stimulation sequences. An original pacing configuration (a) is switched to a modified pacing configuration (b) in a direction opposite to that of an optimization of the hemodynamic parameters, to cause an immediate change in the response to controlled stimulation of the myocardium. This response is assessed based on: the maximum value (P (b, a)) achieved by the peak-to-peak (PEA (i)) of the first peak of endocardial acceleration (PEA) after a pacing configuration change, the mean PEA value (A (b, a)) after stabilization, the PEA variability (V (b, a)) around this average value, and the duration (T (b, a)) of stabilization after the pacing configuration change.

9 Claims, 2 Drawing Sheets

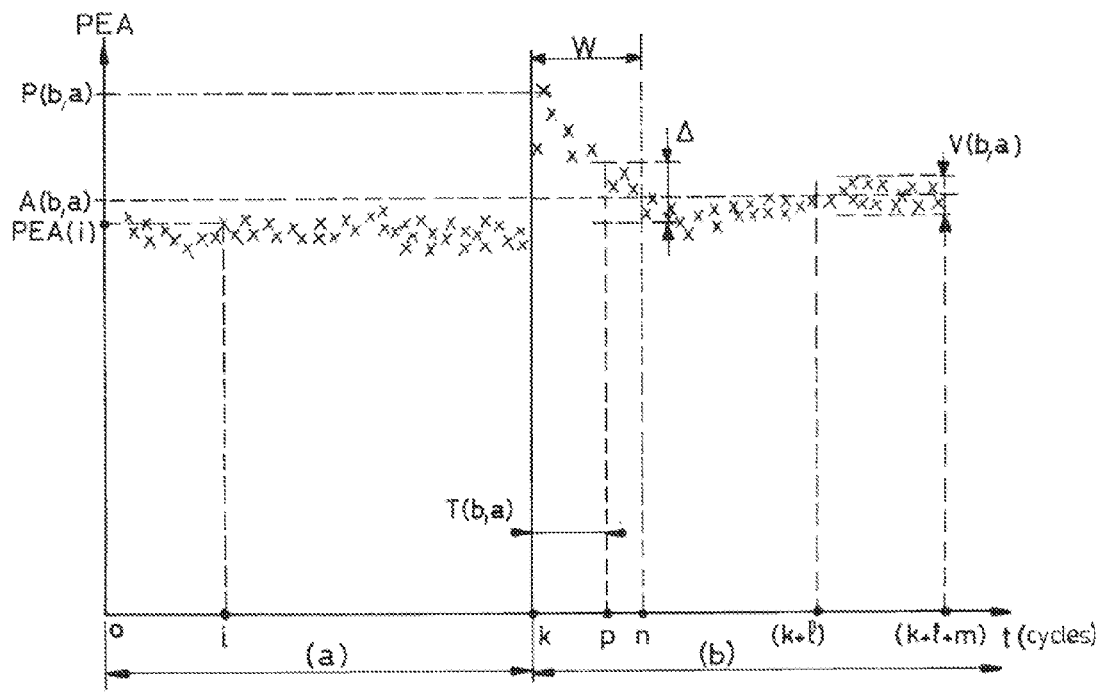

IMPLANTABLE CARDIAC PROSTHETIC FOR RESYNCHRONIZATION BY BIVENTRICULAR PACING USING REVERSE REMODELING

FIELD

The present invention is directed to "active implantable medical devices" as defined by the 20 Jun. 1990 Directive 90/385/EEC of the Council of the European Communities, and more particularly to devices that continuously monitor a patient's heart rhythm and deliver to the heart, if necessary, electrical pulses for joint and permanent stimulation of the left and the right ventricles, so as to resynchronize them, said technique being known as cardiac resynchronization therapy ("CRT") or bi-ventricular pacing ("BVP").

BACKGROUND

A CRT pacemaker is a known device, for example, as disclosed in EP1108446A1 and its counterpart U.S. Pat. No. 6,556,866 (both assigned to Sorin CRM S.A.S, previously known as ELA Medical). A CRT pacemaker is an active implantable medical device that provides CRT and applies an interventricular delay ("VVD") between the respective instants of stimulation of the left and right ventricles. The VVD is adjusted to resynchronize the contractions of both ventricles to optimize the patient's hemodynamic status.

In this regard, a simultaneous stimulation of both ventricles is not always optimal as it does not necessarily lead to a synchronous contraction of both ventricles. This is because, first, the right and left conduction delays in the myocardium are not the same and may depend on multiple factors. Second, the location of the left ventricular lead makes a difference, depending on whether it is an epicardial lead or implanted into the coronary sinus. It is therefore desirable to establish a VVD between the two stimuli, and to adjust this delay to resynchronize the contraction of the ventricles and thus ensure a fine optimization of hemodynamics. The VVD can be zero, positive (the left ventricle is stimulated after the right ventricle) or negative (the right ventricle is stimulated after the left ventricle).

It should be understood that the stimulation of a ventricle (right and/or left) can be achieved using a single stimulation site, or simultaneously a plurality of sites.

The physical locations of the intracardiac electrodes in relation to myocardial tissue to be stimulated are called "pacing sites". These pacing sites are chosen during implantation, by appropriate positioning of the electrodes after verification of the effectiveness of the selected pacing sites. In some cases, a multisite device will have several electrodes placed in the same cavity, and a change in the pacing site in the cavity is possible simply by an internal switching of the device.

CRT pacemakers typically include a classic "dual chamber" pacing mode in which the device monitors ventricular activity after a spontaneous (detection of a P wave of atrial depolarization) or stimulated (application of an A atrial pacing pulse) atrial event. At the same time, the device starts to count a period called "atrioventricular delay" (AVD) such that if no spontaneous ventricular activity (R wave) is detected at the end of this period, then the device triggers a stimulation of the ventricle (application of a V pulse).

Subsequently herein, the term "pacing configuration" means and designates the combination of characteristics relating to i) "pacing sites" (physical position and/or site selection among several possible sites) and ii) setting the VVD and AVD delays.

EP1736203A1 and its counterpart U.S. Pat. No. 7,664,547 (both assigned to Sorin CRM S.A.S, previously known as ELA Medical) discloses a technique for simply, rapidly, automatically assessing the incidence of the various parameters of the CRT therapy, including the AVD and VVD delays, as well as the selection of the pacing sites, so as to optimize the hemodynamic status of the patient.

The device described in this document uses for this purpose the parameters related to endocardial acceleration (EA) to determine the optimal pacing configuration, either at the time of implantation or subsequently. The endocardial acceleration is for example measured by an accelerometer integrated into an endocardial lead, as described for example in EP 0515319A1 and its counterpart U.S. Pat. No. 5,304,208 (both assigned to Sorin Biomedica Cardio SpA).

Indeed, several clinical studies have demonstrated that the endocardial acceleration is a parameter that accurately and in real time reflects the phenomena contributing to the mechanical operation of the myocardium, and thus provides comprehensive information on the cardiac mechanics, both in the case of normal operation and in the case of a deficient one.

To automatically optimize the pacing configuration in a test mode periodically triggered by the implant, EP1736203A1 and its counterpart U.S. Pat. No. 7,664,547 propose to change the current pacing configuration and to determine for each tested pacing configuration a performance index derived from one or more parameters related to the peak endocardial acceleration (PEA), reflecting the effectiveness of the chosen pacing configuration. The pacing configuration eventually chosen is the one that maximizes the performance index.

A comparable technique, using a combination of several specific indexes is disclosed in EP2070562A1 and its counterpart US Patent Publication No. 2009/0157134 (both assigned to Sorin CRM S.A.S, previously known as ELA Medical).

All the techniques described in these documents are intended to determine an optimal pacing configuration, that is to say a configuration that at some point in the therapy, improves the patient's hemodynamic parameters, especially to increase the myocardium contractility and improve the filling of the cavities and consequently the cardiac output.

The present invention, unlike these prior known techniques, does not seek to determine an optimal pacing configuration. The invention instead relates to a phenomenon called "cardiac remodeling", which can be defined as the changes of the heart in response to a disease, and is usually associated with a declining patient condition.

Cardiac remodeling is manifested in the long run by an increase in the size of the left ventricle, with a worsening of the ejection fraction and of the intraventricular pressure regime due to the decrease in contractility and/or too high a blood pressure downstream, and in particular a reduction in cardiac output with serious consequences on the body by progression of heart failure.

By stimulating the ventricles in a controlled manner in at least two points, the CRT therapy optimizes the contraction/relaxation cycle, with a direct benefit by facilitating the work of the heart, but without any regression of the previous changes that occurred because of remodeling. In addition, some patients see no significant response to the CRT stimulation, so that CRT therapy does not benefit them.

To reverse the effects of cardiac remodeling, it has been suggested to employ drug therapy, including treatment with beta blockers, as well as non-drug methods including some surgical techniques for reconstruction of the left ventricle, or the use of certain passive mechanical restraint medical devices or cardiac mechanical assistance devices.

OBJECT AND SUMMARY

It is therefore an of the present invention to find an operating mode of a CRT pacemaker that efficiently overcomes the deleterious consequences of cardiac remodeling.

Essentially, the present invention is directed to a temporary alteration of the pacing configuration in a direction that is contrary to an optimization of the hemodynamic parameters of the patient. This is done to cause an immediate change in the hemodynamic response of the myocardium to the controlled stimulation, and to force the heart to "react" and seek to adapt to this non-optimal pacing mode, resulting in an improvement in contractility and, in the long run, in the morphology of the heart. In other words, the specific BVP stimulation produces a reverse remodeling by slow alteration (several months) of the physiological response of the heart under the stress of such a non-optimized stimulation.

In a first aspect of the invention, the transient response of the patient's heart to the pacing configuration change is obtained and analyzed to assess the more or less great reactivity of the myocardium at any given sudden (deliberate) pacing configuration change in order to find among several possible pacing configurations the one which—if permanently applied—would potentially be the most harmful.

In one embodiment, the present invention uses a hemodynamic sensor such as endocardial acceleration (EA) sensor. Such a sensor is in itself known, but the information it delivers is not used to optimize the cardiac cycles to come—as in the techniques proposed by the prior art devices mentioned above—but instead to select from applied various pacing configurations the one (or ones) that optimizes the reverse remodeling of the heart muscle.

In a second aspect of the invention, the analysis thus carried out defines temporary—occasionally deleterious—pacing configuration sequences that are applied to the myocardium in order to force it to perform a large adaptation over the long term, to improve its response in terms of pressure, ejected volume, filling and ejection timings.

These specific controlled pacing sequences, which preferably last only a few seconds or minutes, have no deleterious effect over the long term, but force the heart to respond in the direction of reverse remodeling, with beneficial consequences that can be found, often within a few days, weeks or months.

In one embodiment, such controlled pacing sequences can be implemented by switching to a changed pacing configuration as "training" (e.g., daily), composed of several successive sequences of this type, with a final return to the original pacing configuration. The sequences of application of a changed pacing configuration are eventually interrupted by periods of recovery, typically with stimulation in the original pacing configuration, before application of another specific training sequence.

Another aspect of the present invention is directed to an implantable medical device for cardiac resynchronization by bi-ventricular pacing, comprising: means for detecting atrial and ventricular events; means for stimulating right and left ventricular pacing sites; means for calculating an atrioventricular delay (AVD); and means for calculating an interventricular delay (VVD). As used herein, the combination of the pacing sites, the AVD and the VVD together define a pacing configuration. The implantable medical device also includes: means for collecting an endocardial acceleration signal, means for measuring the peak-to-peak amplitude of the first peak of endocardial acceleration (PEA) for each cardiac cycle; and switching means for temporarily changing, in a controlled method, the current pacing configuration, from an original pacing configuration to a changed pacing configuration.

In one embodiment, the device further comprises means for assessing, in the changed pacing configuration, a data set including: the maximum amplitude of the PEA reached during a first time period after the change of pacing configuration; the average PEA value, calculated over a predetermined number of cardiac cycles beginning after a second time period following the configuration change; the variability of PEA around said average PEA value; and the length of a third time period after the configuration change. The second time period is selected to allow a stabilization of the patient after the change in pacing configurations, and the third time period is determined as the time it takes the patient to stabilize after the change in pacing configuration.

In one embodiment, the device comprises sequencing means for applying pacing sequences in different pacing configurations, with alternations, during predetermined time periods, between the original pacing configuration and a changed pacing configuration selected from a plurality of possible different changed pacing configurations, the changed pacing configuration being different at each alternation. Preferably, the sequencing means, after each application of a changed pacing configuration and return to the original pacing configuration corresponding to one alternation, maintains the original pacing configuration for a predetermined recovery duration, having a duration that allows the patient to recover.

In one embodiment, the device comprises means for forming a two-input data table giving the said assessed data set for each successively applied pair of pacing configurations {original pacing configuration changed pacing configuration}.

In one embodiment, the device comprises means for designating a representative configuration of the maximum reaction of the myocardium to the configuration change, more preferably a reaction that minimizes the PEA average value compared to the maximum PEA amplitude.

In one embodiment, the duration of the third time period of stabilization after the configuration change is evaluated by determining a short-term PEA average value and a long-term PEA average value and finding the time required for the short-term PEA average value to be within a predetermined permitted deviation from a long-term PEA average value.

In one embodiment, the PEA variability around the PEA average value is evaluated by calculation of a PEA standard deviation over a predetermined number of consecutive cardiac cycles.

DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements, and in which:

FIG. 3 is a timing diagram illustrating the variations in the peak amplitude of the peak endocardial acceleration (PEA)

during successive cardiac cycles, before and after a sudden change in the pacing configuration.

DETAILED DESCRIPTION

An implantable medical device according to a preferred embodiment of the present invention will now be described, with reference to the attached drawings FIGS. 1-3.

The present invention may particularly be applied to implantable medical devices such as those of the Paradym CRT device family, produced and marketed by Sorin CRM, Clamart France, formerly known as ELA Medical, Montrouge, France.

These devices include programmable microprocessor circuitry with digital memory, registers, and control software and analog and digital signal processing circuit components to receive, format, and process electrical signals collected (detected) by implanted electrodes and deliver electrical pulses to these electrodes for stimulation of the myocardium. It is possible to transmit by telemetry software instructions that will be stored in a memory of the implantable device and thereafter executed to implement the functions of the invention that will be described herein. The adaptation of the known CRT devices to implement the functions and features of the present invention is believed to be within the abilities of a person of ordinary skill in the art, and therefore will not be described in detail.

One embodiment of the present invention is based on the analysis of endocardial acceleration (herein "EA"), which is a parameter that accurately and in real time reflects the phenomena contributing to the mechanical operation of the myocardium and may be measured by an accelerometer coupled to the heart muscle, as described for example in EP0515319 A1 (counterpart U.S. Pat. No. 5,304,208) (Sorin Biomedica Cardio SpA). This document teaches a useful method to collect an EA signal through an endocardial lead equipped with a stimulation distal electrode implanted in the atrium or in the ventricle and integrating a microaccelerometer for measuring the EA, and is incorporated herein by reference in its entirety.

It should be understood however that, although in the present description it is mainly referred to the analysis of an EA signal delivered by a sensor placed on an endocardial lead, the invention is also applicable to an analysis conducted using an EA signal delivered by other types of implanted sensors, such as cardiac wall motion sensor, epicardial sensor or an accelerometer placed in the case of an implant. The invention is also applicable to the analysis of a noninvasively collected external EA signal, e.g. from a sensor attached to the patient's chest at the sternum.

Figure 1:
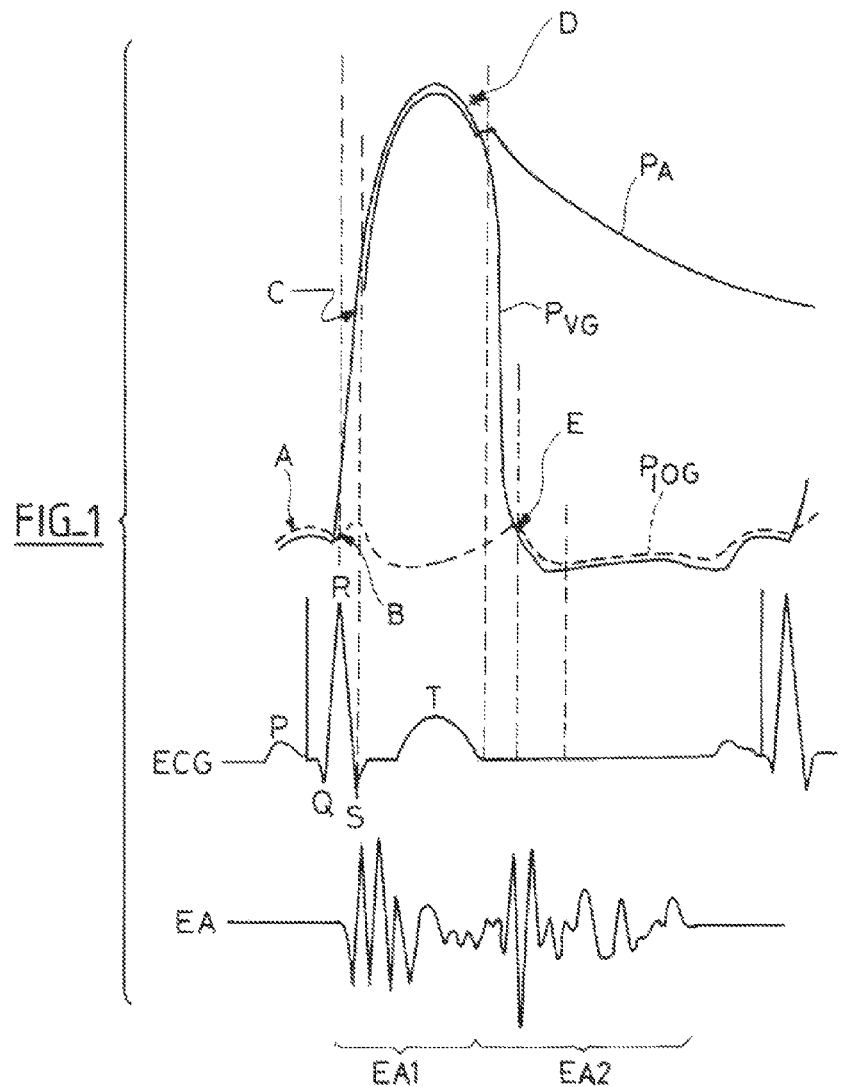
FIG. 1 illustrates the different signals characterizing the activity of the heart during a cardiac cycle, including a surface electrocardiogram ("ECG") record and the corresponding variations in the endocardial acceleration ("EA") signal.

FIG. 1 illustrates the different signals characterizing the activity of the heart during a cardiac cycle, with: at the top, the profile of intracardiac pressures ($P_A$, $P_{VG}$ and $P_{OG}$), in the middle, a record of surface electrocardiogram (ECG), and at the bottom, the variations of the endocardiac acceleration (EA) signal. The characteristic $P_A$ shows the variations in the aortic pressure, $P_{VG}$ shows the variations in the left ventricular pressure, and $P_{OG}$ shows the variations in the left atrium. Points A to E correspond to the different following phases: A is contraction of the left atrium, B is closure of the mitral valve, C is opening of the aortic valve, D is closure of the aortic valve, E is opening of the mitral valve. The ECG signal has successively the P wave corresponding to the depolarization of the atria, the QRS wave complex corresponding to the depolarization of the ventricles and the T wave of ventricular repolarization. The EA signal collected during a given cardiac cycle forms two main components, corresponding to the two major heart sounds (S1 and S2 sounds of phonocardiogram) that can be recognized in each cardiac cycle:

the EA1 component, starting after the QRS complex is caused by a combination of the closure of the atrioventricular valves, the opening of the semilunar valves and the contraction of the left ventricle. The amplitude variations of the EA1 component are closely related to the changes in pressure in the ventricle (the maximum peak to peak amplitude being specifically correlated with the positive maximum of dP/dt pressure variation in the left ventricle) and thus can provide a parameter representative of the myocardium contractility, which is itself linked to the level of activity of the sympathetic system; and the EA2 component occurs during the phase of isovolumetric ventricular relaxation. It accompanies the end of ventricular systole and is mainly produced by the closure of the aortic and pulmonary valves.

Figure 2:
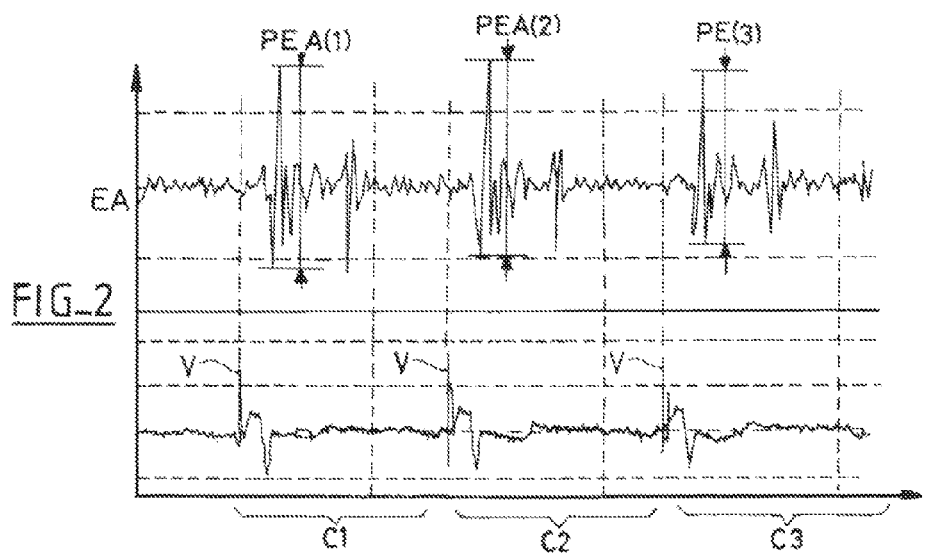
FIG. 2 is a timing diagram showing the variations of the endocardial acceleration EA signal during three consecutive cardiac cycles.

FIG. 2 illustrates the variations in the EA signal on three successive cycles C1, C2, C3.

Markers representative of the beginning of the cardiac cycle can be used to separate successive cardiac cycles in the EA signal that is continuously collected, and thus isolate, bounded in time, EA sub-signals corresponding to a period of one cardiac cycle. In the case of an EA signal based on an endocardial sensor, these temporal markers of the beginning of the cycle may be provided by the device itself, which, according to the pacing mode of operation of the device, stores the moment of V pacing (as illustrated on the ECG plot at the bottom of FIG. 2), or the moments of the R wave detection, as the case may be.

The device then measures the peak to peak amplitude of the peak of endocardial acceleration EA (herein "PEA") on the cycle i, denoted PEA(i).

FIG. 3 illustrates the evolution of this measure PEA(i) over time, cycle after cycle. Specifically, the variations of PEA(i) are shown during the course of a pacing configuration change, from an original pacing configuration, denoted a to a specific changed pacing configuration, denoted b, the configuration change occurring at cycle k.

As previously defined, the "pacing configuration" is understood as the combination of characteristics relating to i) the "pacing sites" (physical position and/or site selection among several possible sites) and ii) the setting of the VVD and AVD delays.

The abrupt change in the pacing configuration at cycle k leads to a physiological response of the myocardium, for example, as shown in FIG. 3, an increase of the PEA amplitude then a gradual stabilization of this amplitude to a slightly higher average value (in the example shown) than in the previous pacing configuration.

The device evaluates the following data, resulting from the sudden transition from pacing configuration a to pacing configuration b:

P(b, a): the maximum value of PEA reached over a time period (or window) W after the pacing configuration change. This maximum value is considered in the window W between cycles k (configuration change) and n, (n−k) defining the width of the window W, typically (n−k)=10 cycles;

A(b, a): the average value of the PEA, calculated for a predetermined number of cardiac cycles beginning after a stabilization period following the configuration change. This average is evaluated over a predetermined number of cycles m after the amplitude of the PEA is stabilized, typically m=10 cycles;

T (b, a): the duration of stabilization after the pacing configuration change. The criterion for such stabilization can be defined as the time between the moment (time k) of the pacing configuration change from pacing configuration a to pacing configuration b until the moment a short-term average (e.g., on four consecutive cycles) of the PEA is equal to, or within, a predetermined percentage of, a long-term average (e.g., on 30 consecutive PEA cycles: If this criterion is met during cycle p, the stabilization time T(b, a) is thus defined as the duration (p–k), typically expressed in number of cycles; and V (b, a): the PEA variability around the mean value of A (b, a) after stabilization.

This information is for example obtained by a calculation of standard deviation performed on m consecutive cycles performed between cycles (k+l) and (k+l+m), it being assumed that after the cycle (k+l) the PEA amplitude in all cases is considered stabilized around its mean value A(b, a). The result is a quadruplet of data (a data set) {P (b, a), A (b, a), T (b, a), V (b, a)}, representative of the transition from pacing configuration a to pacing configuration b.

These steps are automatically or manually repeated for one or more other pacing configurations, and a corresponding table is drawn up, actually or logically in memory, giving for each transition from one original pacing configuration (in column) to a changed pacing configuration (in line), the corresponding quadruplets {P, A, T}:

|  | Configuration #1 | Configuration #2 | Configuration #3 |
|---|---|---|---|
| Configuration #1 | — | {P, A, T, V} (2, 1) | {P, A, T, V} (3, 1) |
| Configuration #2 | {P, A, T, V} (1, 2) | — | {P, A, T, V} (3, 2) |
| Configuration #3 | {P, A, T, V} (1, 3) | {P, A, T, V} (2, 3) | — |

From this table it is possible to analyze the data and choose the most efficient pacing configurations, that is to say, those provoking the most significant response of the heart following the change from the original to the specific changed pacing configuration.

This selection can then be used to define a "training program" of applying on a regular basis, e.g. once a day, a series of changes in the pacing configuration for a specific duration and in a specific order.

In a preferred embodiment, specific changed configurations can be applied (configurations b) for 30 seconds to 1 minute, interspersed with periods of recovery (return to base configuration a) from 1 to 3 minutes.

The choice of the number of changed pacing configurations to be used, the number of changes (alternations) of original to a change pacing configuration and the duration of each specific changed pacing configuration is customizable, notably according to the results reported in the table construed as described above, which compares the effectiveness of the various possible pacing configuration changes.

For example, the expected parameter changes during the mode change can be:

P (b, a): excursion of ±100% compared to the average value of PEA (i) in the configuration a;

T (b, a): about 10 seconds;

A (b, a): about 50% of the average value of PEA (i) in the configuration a, and

V (b, a): about 10% of A (b, a).

Thus, a training program can result in reverse remodeling of the heart, which is beneficial in the long-term. Each training program consists of sequences, each defined by an original pacing configuration a, a temporary specific changed pacing configuration b, a duration of application of this temporary pacing configuration b and a recovery time (return to the original pacing configuration a).

It is possible to program several repetitions of the same sequence, or to schedule a series of different sequences, with a different changed pacing configuration b for each new sequence, or some combination of the foregoing.

Determining the most efficient pacing configurations in terms of reverse remodeling is made according to predetermined criteria, the selected specific changed pacing configuration (configuration b) being for example the one that presents the lowest average amplitude A (b, a) for the highest maximum amplitude P (b, a).

This choice can be done manually by the practitioner by viewing the table mentioned above, or automatically from a predetermined analysis rule applied by the device.

An example of an embodiment of such a program for pacing configuration change sequences will now be described. First, the device triggers the first programmed sequence; if the current pacing configuration is different from the original pacing configuration a, a recovery time is applied in the a mode. At the end of this possible recovery period, the device changes the pacing configuration, from a to b, for a programmed duration. The EA signal is recorded over this period, in order to determine the data set {P, A, T, V} characterizing the pacing configuration transition.

At the end of the programmed duration, the devices returns to the original pacing configuration a, for a prescribed recovery period. At the end of this recovery period, the device triggers the following sequence (or the same or perhaps a different configuration b, as the case may be), or returns to its standard operating mode (original pacing configuration) until the next training phase (e.g. until the next day).

The EA signal is recorded on all the pacing sequences and when the training is completed (end of all sequences), the corresponding data is stored in the device memory and/or transmitted to an external programmer. To provide the practitioner with information on the impact of the training program throughout the day, more data is stored and presented either by daily transmission, or stored in the device memory to be downloaded at the next consultation, through the programmer of the practitioner.

This data is typically the values {P, A, T, V} obtained for each sequence, supplemented by the PEA amplitude reached at the end of the sequence, that is to say, after application of the recovery period. These values may be supplemented by other data stored in a pacing and specific activity configuration, such as: daily measurement at night, activity sensor indicating a patient's rest, and heart rate between the base frequency and 110% of the base frequency. This data enables the practitioner to monitor the impact of training on the heart and evaluate the effectiveness of each training sequence programmed on the sought reverse remodeling.

One skilled in the art will understand the present invention is not limited by, and may be practiced by other than, the foregoing embodiments described, which are presented for purposes of illustration and not of limitation.

The invention claimed is:

1. An active implantable medical device for cardiac resynchronization comprising:

Means for detecting atrial and ventricular events;

Means for applying electrical pulses to preselected stimulation sites of the right and left ventricles;

Means for calculating an atrioventricular delay (AVD);
Means for calculating an interventricular delay (VVD);
wherein a combination of the stimulation sites, the AVD and the VVD together define a pacing configuration;
Means for collecting an endocardial acceleration (EA) signal;
Means for measuring a peak to peak amplitude (PEA (i)) of the first peak of endocardial acceleration (PEA) for each cardiac cycle (i) and
Switching means for changing in a controlled and temporary manner the current pacing configuration, from an original pacing configuration (a) to a changed pacing configuration (b);
Means for assessing, in the changed pacing configuration b, a data set comprising:
  a maximum value (P (b, a)) of the amplitude of the PEA achieved during a first time period after the change of pacing configuration;
  an average value (A (b, a)) of the PEA, calculated for a predetermined number of cardiac cycles starting after a second time period after the pacing configuration change;
  a variability (V (b, a)) of the PEA around said average value of PEA, and
  a duration (T (b, a)) of a third time period after the pacing configuration change corresponding to a stabilization.

2. The device of claim 1, further comprising:
Sequencing means for applying stimulation sequences according to different pacing configurations, with alternation, during predetermined time periods between said original pacing configuration and a changed pacing configuration selected from a plurality of possible different changed configurations.

3. The device of claim 2, further comprising means for maintaining the original pacing configuration for a predetermined recovery period, after each application of a changed pacing configuration b and return to the original pacing configuration a.

4. The device of claim 2 wherein said sequencing means comprises means for selecting a different changed pacing configuration b on each alternation.

5. The device of claim 1, further comprising:
Means for forming a table characterized by said two-input data set evaluated for each successively applied pair (original pacing configuration, changed pacing configuration).

6. The device of claim 1, further comprising:
Means for designating a pacing configuration representative of the maximum reaction of the myocardium to the change of pacing configuration.

7. The device of claim 6, wherein the means for designating a representative pacing configuration further comprises means for designating a pacing configuration minimizing the average value of PEA compared to the maximum amplitude of the PEA.

8. The device of claim 1, further comprising means for evaluating said duration of third time period, after the pacing configuration change by seeking a duration required for a short-term PEA average to be within a predetermined allowed gap of a long-term PEA average.

9. The device of claim 1, further comprising means for assessing the PEA variability around said PEA average value by calculating a PEA standard deviation on a predetermined number of consecutive cycles.

* * * * *